United States Patent [19]

Loose

[11] Patent Number: 5,006,547
[45] Date of Patent: Apr. 9, 1991

[54] TENIDAP AS AN INHIBITOR OF THE RELEASE OF ELASTASE BY NEUTROPHILS

[75] Inventor: Leland D. Loose, Groton, Conn.

[73] Assignee: Pfizer Inc., New York, N.Y.

[21] Appl. No.: 495,888

[22] Filed: Mar. 19, 1990

[51] Int. Cl.$^5$ .............................................. A01H 43/38
[52] U.S. Cl. ..................................... 514/414; 514/418
[58] Field of Search ............................... 514/414, 418

[56] References Cited

U.S. PATENT DOCUMENTS

| | | | |
|---|---|---|---|
| 4,556,672 | 12/1985 | Kadin | 514/414 |
| 4,725,616 | 2/1988 | Kadin | 514/411 |
| 4,853,409 | 8/1989 | Showell | 514/418 |
| 4,861,794 | 8/1989 | Otterness | 514/414 |
| 4,920,127 | 4/1990 | King et al. | 514/278 |

FOREIGN PATENT DOCUMENTS 277738  8/1988  European Pat. Off. .

OTHER PUBLICATIONS

Janoff, A., American Journal of Pathology 68:579–591 (1972).
Johnson, R. J., et al., J. Exp. Med. 168:1169–1174 (1988).
Showell, H. J., et al., J. Reticuloendothelial Society 30:167–181 (1981).
Showell, H. J., et al., Life Sciences 27:421–426 (1980).
Walenga, R. W., et al., Life Sciences 27:1047–1053 (1980).
Serhan, C. N., et al., Biochem. Biophys. Res. Comm. 107:1006–1012 (1982).
Edelson, H. S., et al., "Dissociation by Piroxicam of Degranulation and Superoxide Anion Generation from Decrements in Chlortetracycline Fluorescence of Activated Human Neutrophils", Biochem. Biophys. Res. Commun. 104:247–253 (1982).
Goldstein, I. M., "Agents that Interfere with Archidonic Acid Metabolism", *Inflammation: Basic Principles and Clinical Correlates*, Gallin, J. I.
Goldstein, I. M., and Synderman, R., Eds. (1988) pp. 934–946, Raven Press, New York.
Dunn, T. L. et al., "Solid-Phase Radioimmunoassay for Human Neutrophil Elastase: A Sensitive Method for Determining Secreted and Cell-Associated Enzyme", anal. biochem. 150: 18–25 (1985).
Havemann, K. et al., "Physiology and Pathophysiology of Neutral Proteinases of Human Granulocytes", Adv. Exp. Med. Bio. 167:1–20 (1984).
Abramson, et al., "Modes of Action of Aspirin-Like Drugs", P.N.A.S. 82:7227–7231 (1985).
Turner, R. A., et al., "Effects of Benoxaprofen on Human Neutrophil Function", J. Rheumatology 11:265–271 (1984).
Smolen, J. E., et al., "Effects of Indomethacin, 5,8,11,14–Eicosatetraynoic Acid, and p–Bromophenacyl Bromide on Lysosomal Enzyme Release and Superoxide Anion Generation by Human Polymorphonuclear Leukocytes", Biochem. Pharmacol. 29:533–538 (1980).
Mikulikova, D., et al., "The Effect of Indomethacin and Its Ester on Lysosomal Enzyme Release from Polymorphonuclear Leukocytes and Intracellular Levels of GAMP and cGMP after Phagocytosis of Urate Crystals", Biochem. Pharmacol. 31:460–463 (1982).
Maderazo, E. G., et al., "Inhibition of Human Polymorphonuclear Leukocyte Cell Responses by Ibuprofen", J. Pharmaceutical Sciences 73:1403–1406 (1984).
CA: 110(21) 185555v.
CA: 110(25) 229951y.

*Primary Examiner*—Stanley J. Friedman
*Assistant Examiner*—T. Criares
*Attorney, Agent, or Firm*—Peter C. Richardson; J. Trevor Lumb; Gregg C. Benson

[57] ABSTRACT

This invention relates to the use of tenidap, 5-chloro-2,3-dihydro-2-oxo-3-(2-thienylcarbonyl)-indole-1-carboxamide, and the pharmaceutically-acceptable base salts thereof to inhibit the release of elastase by neutrophils in a mammal. This invention also relates to the use of tenidap and its salts for treating elastase-mediated diseases and dysfunctions such as arteritis, proteinuria and pulmonary emphysema in mammals. The methods of this invention comprise administering an effective amount of tenidap or salts thereof to a mammal.

16 Claims, No Drawings

TENIDAP AS AN INHIBITOR OF THE RELEASE OF ELASTASE BY NEUTROPHILS

BACKGROUND OF THE INVENTION

1. Field of the Invention

This invention relates to the use of tenidap and the pharmaceutically-acceptable base salts thereof for inhibiting the release of elastase by neutrophils in a mammal. Tenidap and its salts are useful for inhibiting the release of elastase by neutrophils in a mammal, per se, and in treating elastase-mediated diseases and dysfunctions in a mammal. Such elastase-mediated diseases and dysfunctions include, but are not limited to, arteritis, proteinuria and pulmonary emphysema. The use of tenidap and its salts comprises administering an effective amount thereof to a mammal.

2. General Background

Tenidap, 5-chloro-2,3-dihydro-2-oxo-3-(2-thienylcarbonyl)-indole-1-carboxamide, has the structural formula

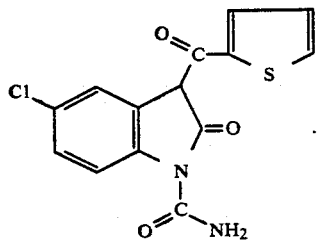

Tenidap, among other 3-substituted-2-oxindole-1-carboxamides are disclosed and claimed in U.S. Pat. No. 4,556,672 which is assigned to the assignee hereof. That patent discloses that those compounds, in addition to being useful as antiinflammatory and analgesic agents, are inhibitors of both cyclooxygenase (CO) and lipoxygenase (LO). The teachings thereof are incorporated herein by reference.

The use of tenidap and its pharmaceutically-accceptable base salts, among certain other 3-substituted-2-oxindole-1-carboxamides, to inhibit interleukin-1 biosynthesis in a mammal and to treat interleukin-1 mediated disorders and dysfunctions is disclosed in U.S. Pat. No. 4,861,794 which is assigned to the assignee hereof.

U.S. Pat. No. 4,853,409, assigned to the assignee hereof, discloses the use of tenidap and its pharmaceutically-acceptable base salts, among certain other 3-substituted-2-oxindole-1-carboxamides, to suppress T-cell function in a mammal and to treat T-cell mediated autoimmune disorders of the systemic or organ specific type.

An anhydrous, crystalline form of the sodium salt of tenidap is disclosed in European Patent Application 277,738, which has been filed in the name of the assignee hereof.

Elastase is a protease which is released by neutrophils in a mammal and mediates certain diseases and dysfunctions. [Janoff, A., American Journal of Pathology 68:579-591 (1972).] Such elastase mediated diseases and dysfunctions include, but are not limited to, arteritis, proteinuria and pulmonary emphysema [Janoff, A., Op. cit. and Johnson, R. J., et al., J. Exp. Med. 168:1169-1174 (1988).]

Until the invention herein, there was no report of use or intent to use tenidap or its salts to inhibit release of elastase by neutrophils in a mammal and to treat elastase-mediated diseases and dysfunctions with such compounds nor any appreciation of their role in such treatments.

SUMMARY OF THE INVENTION

It has been found that tenidap and the pharmaceutically-acceptable base salts thereof inhibit the release of elastase by neutrophils and are useful in inhibiting the release of elastase by neutrophils in a mammal, per se, and in treating elastase-mediated diseases and dysfunctions. Such elastase-mediated diseases and dysfunctions include, but are not limited to, arteritis, proteinuria and pulmonary emphysema.

The methods of using tenidap and its pharmaceutically-acceptable base salts comprise administering to a mammal an effective amount thereof. Administration can comprise any known method for therapeutically providing a compound to a mammal such as by oral or parenteral administration as defined hereinbelow.

DETAILED DESCRIPTION OF THE INVENTION

Tenidap, which has the chemical structure

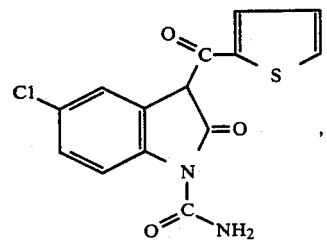

its pharmaceutically-acceptable base salts and the preparation thereof are described in U.S. Pat. No. 4,556,672, the teachings of which are incorporated herein by reference. This invention concerns new uses for tenidap and its salts which comprise methods for inhibiting the release of elastase by neutrophils in a mammal in need thereof. Also within the scope of this invention are methods of treating elastase-mediated disorders and dysfunctions in a mammal which include, but are not limited to, arteritis, proteinuria and pulmonary emphysema.

As disclosed in U.S. Pat. No. 4,556,672, tenidap is acidic and forms base salts. All such base salts are within the scope of this invention and can be formed as taught by that patent. Such suitable salts, within the scope of this invention, include both the organic and inorganic types and include, but are not limited to, the salts formed with ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of bases which form such base salts include ammonia, primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides such as sodium ethoxide and potassium methoxide; hydrides such as calcium hydride and sodium hydride; and carbonates such as potassium carbonate and sodium carbonate. Preferred salts are those of sodium, potassium, ammonium, ethanolamine, diethanolamine and triethanolamine. Particularly preferred is the sodium salt. European Patent Application 277,738, which has been filed in the name of the assignee hereof, discloses an anhydrous, crystalline form of such a salt. The teachings thereof are incorporated herein by reference.

Also within the scope of this invention are the solvates such as the hemihydrates and monohydrates of the compounds hereinabove described.

The methods of this invention comprise administering tenidap and the pharmaceutically-acceptable base salts thereof to a mammal. Such compounds and their salts can be administered to said mammal either alone or, preferably, in combination with pharmaceutically-acceptable carriers or diluents in a pharmaceutical composition, according to standard pharmaceutical practice. Such administration can be oral or parenteral. Parenteral administration as used herein includes, but is not limited to, intravenous, intramuscular, intraperitoneal, subcutaneous, transdermal and topical including, but not limited to oral lavage and inhalation, administration. While it is generally preferred to administer such compounds and their salts orally, other methods may be preferred depending upon the particular elastase-mediated disease or dysfunction being treated.

In general, tenidap and its salts are most desirably administered in doses ranging from about 20 mg up to about 200 mg per day, with a preferred range of about 40 mg up to about 120 mg per day, for oral administration and from about 1 mg up to about 200 mg per day for parenteral administration, although variations will still necessarily occur depending upon the weight of the subject being treated. The appropriate dose for inhibiting the release of elastase by neutrophils in a mammal and for treatment of elastase-mediated disorders and dysfunctions with tenidap and its salts will be readily determined by those skilled in the art of prescribing and/or administering such compounds. Nevertheless, it is still to be appreciated that other variations may also occur in this respect, depending upon the species of mammal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur, provided that such higher dose levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the generally preferred mode of administration of tenidap or its pharmaceutically-acceptable base salts is oral, they may be administered parenterally as well. Such parenteral administration may be the preferred mode of administration for the treatment of certain elastase-mediated diseases or dysfunctions.

For purposes of parenteral administration, solutions of tenidap or a salt thereof in sesame or peanut oil or in aqueous propylene glycol may be employed, as well as sterile aqueous solutions of the corresponding water soluble base salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these injectable solutions to insure that the final products are obtained in a sterile condition. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like. Specific transdermal flux enhancing compositions are disclosed in European Patent Application 271,983 and European Patent Application 331,382, which have been filed in the name of the assignee of this invention, the teachings of which are incorporated herein by reference. For purposes of topical administration, the dosage form of the particular compound may include, by way of example and not of limitation, solutions, lotions, ointments, creams and gels. Further, administration by inhalation can be achieved by menas and methods well known to those skilled in the art. Such means include the use of nebulizers or atomizers whereby a solution of tenidap or a salt thereof is inhaled as a mist.

The ability of the compounds of this invention to inhibit the release of elastase by neutrophils was demonstrated by the assay procedure described in Dunn, T. L., et al., Analytical Biochemistry 150:18–24 (1985) and references cited therein. Neutrophils for the assay were obtain as follows. Whole human blood from normal volunteers was obtained by venipuncture into heparinized syringes. The majority of the red cells were removed by dextran sedimentation and neutrophils were separated by density centrifugation over hypaque ficoll. The neutrophil rich fraction was washed and residual red cells were removed by hypotonic lysis according to the procedure described by Blackburn, W. D. et al., Arthritis Rheum. 30:1006–1014 (1987). The neutrophils so prepared were used in the assay described below and cell viability was assured by determining their ability to exclude typan blue. In each assay the cell viability routinely exceeded 95%.

Affinity purified anti-human neutrophil elastase (anti-HNE) antibody was labeled with carrier free $^{125}$I-Na by using a modification of the lactoperoxidase method of Marchelonis, J. J., Biochem. J. 113:229–305 (1969). Generally, 10 μg quantities of protein were labeled to an initial specific activity of $2.2 \times 10^{-5}$ mCi/ng. Free iodine was separated from bound $^{125}$I by Sephadex G-25 column chromatography. The $^{125}$I-labeled anti-HNE was aliquoted and stored at $-70°$ C. for up to one month prior to use.

Neutrophil cell suspensions, prepared as described above, were incubated at 37° C. for 15–30 minutes in the presence of varying concentrations of tenidap. Tenidap was dissolved and diluted in water and added to the cells directly therefrom. After the cells had been incubated in the presence of tenidap, the cell suspensions ($5 \times 10^6$ cells/ml, 125 μl well) were added to IgG coated and bovine serum albumin (BSA) blocked wells of microtiter plates and incubated for 45 minutes at 37° C. As controls, similar incubations were performed in the absence of IgG. Following incubation, the cell suspensions were centrifuged (750×g) for 5 minutes at 4° C.

DE-52 cellulose-purified IgG fraction goat anti-HNE (10 mg/ml), diluted at 1/1000 in PBS, was used to coat vinyl assay wells (125 μl) for 4 hours at 25° C. The wells were then blocked with PBS-1% BSA (100 μl) for 1 hour at 25° C. to eliminate nonspecific binding, washed with PBS three times and 100 μl samples of the supernatants obtained as described above were then added to each well and allowed to incubate 16 hours at 25° C. Standard curves were generated with serial dilutions of the DFP inactivated enzyme (500 μg/ml) in PBS-1% BSA. After three washings with PBS, affinity purified $^{125}$I-labeled anti-HNE was added to each well (100,000 cpm/100 μl). The wells were incubated for 16 hours at 25° C. and washed three times with PBS and each well was counted for 1 minute in a gamma counter. $^{125}$I-Anti-HNE (cpm bound)$\times 10^{-3}$ was plotted against protein concentration in nanograms per milliliter. Standard binding curves using other purified proteins instead of HNE were used as described above.

What is claimed is:

1. A method of inhibiting the release of elastase by neutrophils in a mammal in need thereof which comprises administering to said mammal an elastase release inhibiting amount of tenidap or a pharmaceutically-acceptable base salt thereof.

2. The method according to claim 1 wherein tenidap or a pharmaceutically-acceptable base salt thereof is administered orally.

3. The method according to claim 1 wherein tenidap or a pharmaceutically-acceptable base salt thereof is administered parenterally.

4. A method of treating an elastase-mediated disease or dysfunction in a mammal which comprises administering to said mammal an elastase-mediated disease or dysfunction treating, amount of tenidap or a pharmaceutically-acceptable base salt thereof.

5. The method according to claim 4 wherein tenidap or a pharmaceutically-acceptable base salt thereof is administered orally.

6. The method according to claim 4 wherein tenidap or a pharmaceutically-acceptable base salt thereof is administered parenterally.

7. The method according to claim 4 wherein the elastase-mediated disease or dysfunction is arteritis.

8. The method according to claim 5 wherein the elastase-mediated disease or dysfunction is arteritis.

9. The method according to claim 6 wherein the elastase-mediated disease or dysfunction is arteritis.

10. The method according to claim 4 wherein the elastase-mediated disease or dysfunction is proteinuria.

11. The method according to claim 5 wherein the elastase-mediated disease or dysfunction is proteinuria.

12. The method according to claim 6 wherein the elastase-mediated disease or dysfunction is proteinuria.

13. The method according to claim 4 wherein the elastase-mediated disease or dysfunction is pulmonary emphysema.

14. The method according to claim 5 wherein the elastase-mediated disease or dysfunction is pulmonary emphysema.

15. The method according to claim 6 wherein the elastase-mediated disease or dysfunction is pulmonary emphysema.

16. The method according to claim 15 wherein tenidap or a pharmaceutically-acceptable base salt thereof is administered by inhalation.

* * * * *